United States Patent [19]

Shoesmith

[11] Plant 4,563

[45] Jul. 1, 1980

[54] YELLOW CHRYSANTHEMUM NAMED MEDALIST

[75] Inventor: Leonard H. Shoesmith, Woking, England

[73] Assignee: Pan-American Plant Company, West Chicago, Ill.

[21] Appl. No.: 17,407

[22] Filed: Mar. 5, 1979

[51] Int. Cl.[2] ..... A01H 5/00

[52] U.S. Cl. ..... Plt./78

[58] Field of Search ..... Plt./78, 75

*Primary Examiner*—Robert E. Bagwill

*Attorney, Agent, or Firm*—Charles W. Rummler

[57] ABSTRACT

A new cultivar of *Chrysanthemum morifolium* distinguished by the bright yellow color of its flat blooms which have a green center in the mass of its yellow disc florets. This greenhouse pot plant is also distinguished by its compact habit and the distinct advantage that it will not heat delay. It is a late nine-week medium variety and is at its best when grown from April to October.

1 Drawing Figure

BACKGROUND OF THE NEW PLANT

My new yellow chrysanthemum originated as a seedling of unknown parentage discovered by me in 1974 while growing in greenhouse at West Chicago, Ill., U.S.A., among a group of similar plants maintained as part of a breeding program begun in 1973. This plant, following my discovery, was selected by me and propagated at West Chicago, Ill., by cuttings from the original plant. Propagation of this new plant through several successive generations has shown that its distinctive characteristics hold true from generation to generation and appear to be firmly fixed. Commercial scale propagation of this plant is now being carried on at West Chicago, Ill., by means of cuttings.

DESCRIPTION OF THE DRAWINGS

My new yellow chrysanthemum is illustrated by the accompanying two sheets of drawings, of which the first is a photographic view showing a potted plant in full bloom, the photograph having been hand painted to show the true colors of the flowers; and the second sheet is a print of a photocopy of typical leaves of this variety at several stages of maturity.

DESCRIPTION OF THE NEW PLANT

The following is a detailed description of my new chrysanthemum plant based upon observations of greenhouse plants made in 1978 at West Chicago, Ill., the color designations being according to The R.H.S. Colour Chart published by The Royal Horticultural Society of London, England.

THE PLANT

Origin: Seedling.
Parentage: Unknown.
Classification: Botanic — *Chrysanthemum morifolium.*
Commercial — greenhouse pot plant.
Form: Perennial herbaceous bush.
Height: 11 to 12 inches.
Growth: Vigorous, strong and upright.
Foliage: Quantity — abundant.
*Leaf size.*—Pot plant average.
*Leaf shape.*—Deltoid with cleft margin.
*Surface aspect.*—Canescent.
*Color.*—Upper side — 147A. Under side — 147B.

*Venation.*—Pinnately veined.
*Petioles.*—Length — about ½ to ¾ inch.

THE BUD

Size: The bud size varies in both diameter and length.
Shape: Globular.
Opening rate: Normal.
Color: When phyllaries first divide — 151B. When petals begin to unfurl — 154B.
Phyllaries: Number — about 40.
*Shape.*—Lanceolate.
*Color.*—146C.
Peduncle:
*Character.*—Rigid and erect.
*Surface aspect.*—Canescent.
*Color.*—146C.

THE FLOWER

Recommended season: April to October.
Response: 9 weeks.
Blooming habit: Intermittent.
Blooms:
*Flower type.*—Composite.
*Size.*—Medium.
*Borne.*—In a cyme.
*Shape.*—When bloom first opens—flat. As bloom matures — the form remains flat.
*Florets.*—Numerous.
*Arrangement.*—Imbricated.
*Form.*—Oblanceolate with narrow acute apex and entire margin.
*Texture.*—Soft.
*Appearance.*—Satiny.
*Color.*—Outer florets: Top side — 9A. Reverse side — 9C. Inside florets: Top side — 2A. Reverse side — 2B. Center of disc — green.
Peduncle:
*Length.*—About 8 to 10 inches.
*Strength.*—Strong and upright.
*Color.*—146C.
Discoloration after full bloom: None.
Persistence: The florets hang on and dry.
Fragrance: Typical chrysanthemum.
Lasting quality: On plant — 3 weeks. As cut flower — not recommended.

REPRODUCTIVE ORGANS

Stamens: Number — 5. Arrangement — syngenesious.
*Anthers.*—Size — insignificant.
*Filaments.*—Length — insignificant. Color: yellow.
*Pollen.*—Color — yellow.
Pistils: Number — one for each ray and disc floret.
*Styles.*—Length — insignificant. Color: yellow.
*Stigmas.*—Color — yellow.
Ovaries: Inferior, bicarpellate.

This new chrysanthemum pot plant is particularly distinquished by its compact growth habit and a bright yellow flower of medium size which has a green center in its mass of disc florets. The flowers are composite and rather flat with several rows of ray florets which give an attractive full appearance. This plant is a late nine-week medium variety, at its best when grown from April to October, and has the advantage that it will not heat delay.

I claim:

1. A new and distinct chrysanthemum cultivar, substantially as herein shown and described, characterized by its bright yellow composite flowers which have green florets at the center of the disc, by its compact plant habit, and by its freedom from heat delay.

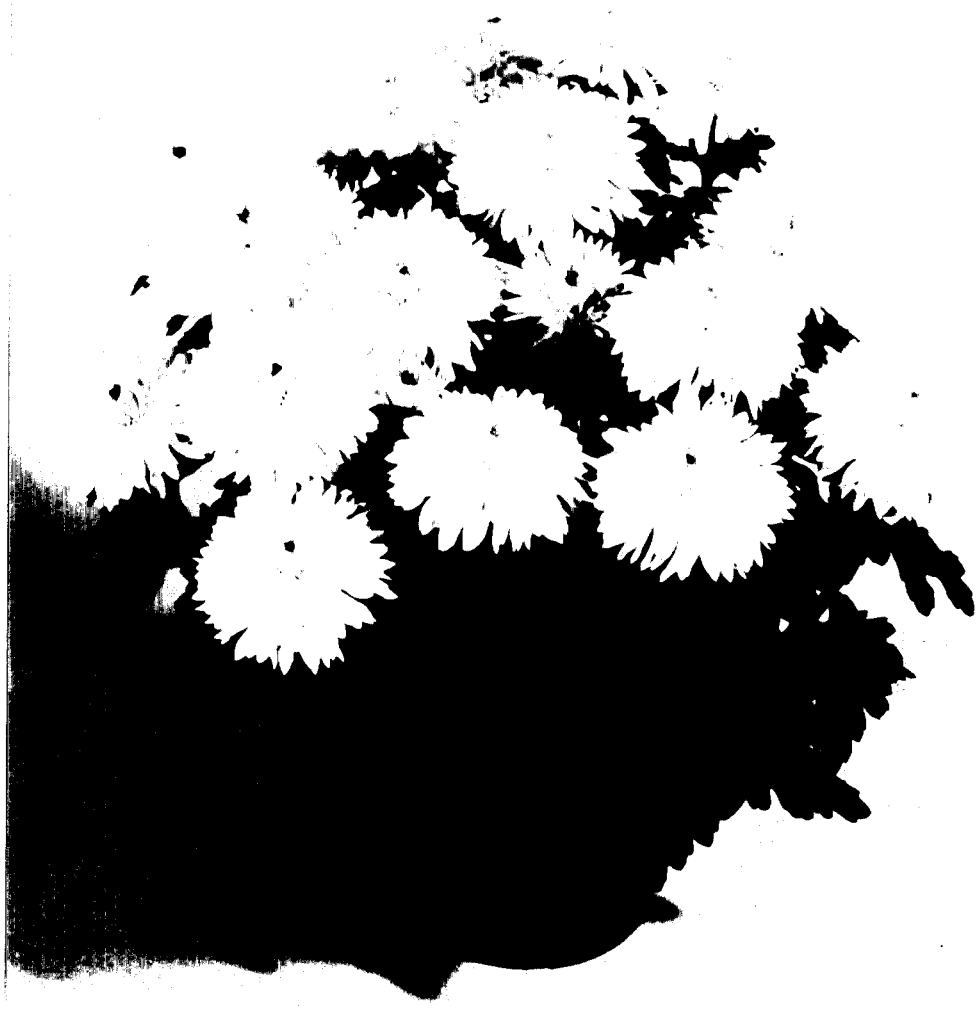

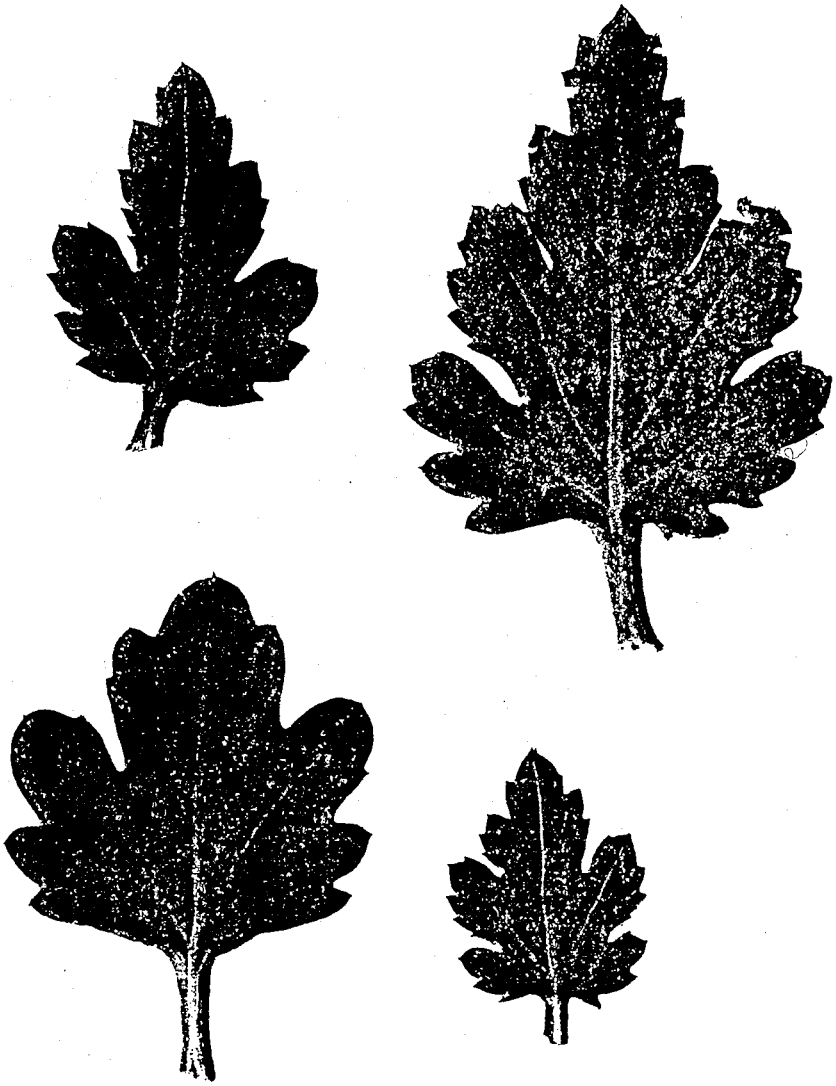

* * * * *